United States Patent [19]

Swaine

[11] Patent Number: 4,783,481
[45] Date of Patent: Nov. 8, 1988

[54] RODENTICIDES

[75] Inventor: Harry Swaine, Berkshire, England

[73] Assignee: Imperial Chemical Industries PLC, London, England

[21] Appl. No.: 896,579

[22] Filed: Aug. 18, 1986

Related U.S. Application Data

[63] Continuation of Ser. No. 675,402, Nov. 27, 1984, abandoned.

[30] Foreign Application Priority Data

Dec. 14, 1983 [GB] United Kingdom ............... 8333334

[51] Int. Cl.$^4$ ............................................. A01N 43/16
[52] U.S. Cl. ................................................. 514/457
[58] Field of Search .................................. 514/457

[56] References Cited

U.S. PATENT DOCUMENTS

| | | | |
|---|---|---|---|
| 3,764,693 | 10/1973 | Bojchetti et al. | 514/457 |
| 4,035,505 | 7/1977 | Hadler et al. | 514/457 |
| 4,520,007 | 5/1985 | Entwistle et al. | 424/84 |

FOREIGN PATENT DOCUMENTS

| | | | |
|---|---|---|---|
| 742290 | 5/1970 | France | 514/457 |
| 2126578 | 3/1984 | United Kingdom . | |

OTHER PUBLICATIONS

Hadler et al., Nature (Lond), 253, pp. 275-277 (1975).
Dubock et al., "Brodifacoum (TALON Rodenticide), A Novel Concept", Paper Presented at 8th Vertibrate Pest Conference, Sacramento, Co. Mar. 1978.
Meehan, A. P., Rats and Mice, Their Biology and Control (Rentokil Library, 1984) at pp. 151-8.

Primary Examiner—Allen J. Robinson
Attorney, Agent, or Firm—Cushman, Darby & Cushman

[57] ABSTRACT

Rodenticidal compositions comprising a rodenticidally effective amount of an isomer of a 3-substituted-4-hydroxycoumarin rodenticide which is capable of existing in more than one stable isomeric form. The isomer, for example, the trans isomer of brodifacoum, is significantly less persistently retained in the tissues of non-rodent mammalian or avian species likely to consume the composition or poisoned rodent carcasses than other isomers of the same 3-substituted-4-hydroxycoumarin. The compositins are substantially free of such other isomers, e.g., the cis isomer of brodifacoum, thereby reducing the risk to non-target species from accidental ingestion.

3 Claims, No Drawings

RODENTICIDES

This is a continuation of application Ser. No. 675,402 filed Nov. 27, 1984, now abandoned.

This invention relates to improved rodenticidal compositions and their use in combating rodent pests.

Various anticoagulant rodenticides have been previously described including for example those based on 3-substituted-4-hydroxycoumarins such as Warfarin, bromadiolone, defenacoum and brodifacoum. Of these brodifacoum has become one of the most successful and widely used rodenticides because of its ability to control Warfarin-resistant rodents and its ability to kill rodents who have only consumed a single dose.

Unfortunately, the use of rodenticides poses a threat to the safety and survival of other non-target mammalian and bird-species e.g. those that accidentally consume the poisoned bait laid in a rodent control operation or carrion feeders such as foxes, cats, hawks and owls, and domestic animals, which may consume dead or moribund rodents which have themselves received a dose of rodenticide. These undesirable side effects of the use of rodenticides have been reviewed by A. P. Meehan in "Rats and Mice—their biology and control" (Rentokil Library, 1984) at pages 151–8.

It has therefore been an object of rodenticide research over the years to produce a product which will effectively control a variety of rodent pests whilst minimising the risks to non-target species arising from accidental ingestion of the poison. Usually this has been attempted by concealing the bait in a feeding station which is accessible to the rodents but not to the other species. This however does not protect those animals which eat the carcasses of poisoned rodents.

The present invention concerns improved rodenticidal compositions which retain their rodenticidal effectiveness but which present a much reduced risk to non-rodent species which may come into contact with poisoned bait or poisoned rodents' carcasses.

Rodenticides of the defenacoum and brodifacoum type exist as a mixture of cis and trans isomers (see for example M. R. Hadler et al, Nature (Lond), 253, pp. 275–277 (1975), A. C. Dubock et al, "Brodifacoum (TALON Rodenticide), A novel concept", Paper presented at 8th Vertibrate Pest Conference, Sacramento, California, USA, March 1978). In terms of rodenticidal effectiveness there appears to be little difference between the isomers—thus Dubock et al (loc. cit) states for brodifacoum "there is no significant difference in anticoagulant potency, resistance, acute oral $LD_{50}$ or rate of kill of the two isomers when tested against albino mice, albino rats and homozygous resistant rats". Consequently technical brodifacoum as used hitherto in the formulation of rodenticidal products such as baits has comprised from 90 to 100% by weight mixed cis and trans isomers, usually consisting of from about 55 to about 72% by weight of the cis isomer, the remainder being the trans isomer.

We have now discovered that although there is little to choose between the isomers in terms of their rodenticidal effectiveness there is a significant difference in their persistence in the tissues of nonrodent non-target species which may be exposed to accidental ingestion of brodifacoum. In particular we have shown that in many such species which have received doses of the mixed isomers in approximately equal proportions (ca. 50:50) apparently selective metabolism of most or all of the trans isomer takes place before death occurs, such death presumably being due to the relatively metabolically more stable cis isomer.

These observations have led to the development of the present invention which may be expressed broadly as providing an improved rodenticidal composition comprising a rodenticidally effective amount of an isomer of a 3-substituted-4-hydroxycoumarin capable of existing in more than one stable isomeric form characterised in that the isomer is one which when compared with any other isomer or isomers of the same 3-substituted-4-hydroxycoumarin is significantly less persistently retained in the tissues of non-rodent mammalian or avian species likely to consume either rodenticidal bait formulations or poisoned rodent carcasses the composition being substantially free of the other isomer or isomers.

Typical rodenticidally active 3-substituted-4-hydroxycoumarins which are useful in the present invention include the significantly less persistently retained stable isomeric forms of compounds described in U.S. Pat. Nos. 3,764,693, 4,035,505 and published UK patent application No. 2126578A, the disclosures of which are herein incorporated by reference. Preferably the 3-substituted-4-hydroxycoumarins are those having either the general formula I:

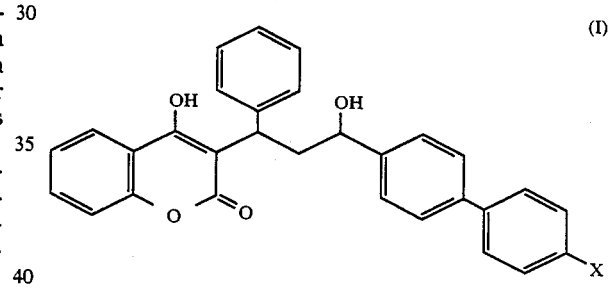

wherein X is hydrogen or halogen, especially chloro or bromo, or the general formula II:

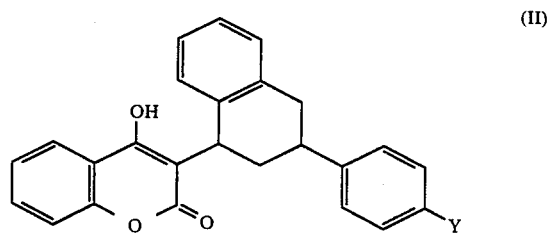

wherein Y is trifluoromethyl, phenyl, 4-bromophenyl, 4-chlorophenyl, 4-trifluoromethylphenyl, 4-cyanophenyl, 4-trifluoromethylphenoxy, 4-cyanophenoxy, or 4-trifluoromethylbenzyloxy.

Of particular interest is the compound of formula I wherein X is bromo, and the compounds of formula II wherein Y is phenyl, 4-bromophenyl or 4-trifluoromethylbenzoyloxy.

Isomerism exists in the compounds of formula I and formula II because of the presence of two chiral centres, arising from the two assemmetrically substituted carbon atoms indicated by asterisks in the formula IA and IIA below.

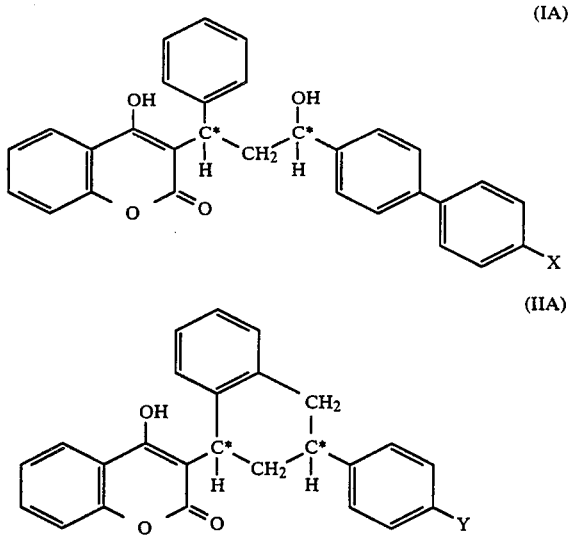

Each asymmetrically substituted carbon atom may therefore exist in either the S- or R- absolute configuration giving rise to the possibility of four isomeric forms of the compounds (two pairs of diastereoisomers) which may be designated as (S,S), (S,R), (R,S) and (R,R). Of these, the (S,S) and (R,R) forms are a first pair of enantiomers and the (R,S) and (S,R) forms are a second pair of enantiomers.

Hitherto these compounds have been prepared and used hitherto for rodenticidal purposes in the form of a mixture of all four isomers, each enantiomeric pair of isomers being present in racemic proportions, although the ratio of the first pair to the second pair in such products may have varied from about 3:1 to about 1:3.

In any compound of formula II the correlation between the absolute stereochemical definition and the geometrical isomerism is believed to indicate that the so-called cis-isomer is in fact the racemic mixture of the (S,R) and (R,S) isomers and the trans-isomer is in fact the racemic mixture of the (S,S) and (R,R) isomers. Thus the compound brodifacoum as manufactured and used hitherto consists of a mixture of the four isomers which may be designated as:

3R-(4'-bromobiphenyl-4-yl)-1S-(4-hydroxycoumarin-3-yl)-1,2,3,4-tetrahydronaphthalene (isomer A).
3S-(4'-bromobiphenyl-4-yl)-1R-(4-hydroxycoumarin-3-yl)-1,2,3,4-tetrahydronaphthalene (isomer B).
3R-(4'-bromobiphenyl-4-yl)-1R-(4-hydroxycoumarin-3-yl)-1,2,3,4-tetrahydronaphthalene (isomer C), and
3S-(4'-bromobiphenyl-4-yl)-1S-(4-hydroxycoumarin-3-yl)-1,2,3,4-tetrahydronaphthalene (isomer D).

Thus isomer A and isomer B represent the (R,S) and (S,R) racemic pair of enantiomers corresponding to cis-brodifacoum and isomer C and isomer D represent the (S,S) and (R,R) racemic pair of enantiomers corresponding to trans-brodifacoum.

In the case of a compound of formula I because there is no restriction of rotation of the bonds between the two chiral centres there is no stable cis or trans isomerisation as such. However, when the atoms are disposed in the same relative configuration as the compounds of formula II then the absolute stereochemical designation can be assigned, and it can be shown that the (S,S) and (R,R) pair of enantiomers for a compound of formula I corresponds to the (S,R) and (R,S) pair (i.e. the cis-isomer) of a compound of formula II, and similarly the (S,R) and (R,S) pair of enantiomers for a compound of formula I corresponds to the (S,S) and (R,R) pair (i.e. the trans isomer of a compound of formula II. Thus the compound bromadiolone as manufactured and used hitherto consists of a mixture of the four isomers which may be designated as:

1-(4'-bromobiphenyl-4-yl)-3-(4-hydroxycoumarin-3-yl)(1R,3R)-propanol (isomer A')
1-(4'-bromodiphenyl-4-yl)-3-(4-hydroxycoumarin-3-yl)(1S,3S)-propanol (isomer B')
1-(4'-bromobiphenyl-4-yl)-3-(4-hydroxycoumarin-3-yl)(1S,3R)-propanol (isomer C')
1-(4'-bromobiphenyl-4-yl)-3-(4-hydroxycoumarin-3-yl)(1R,3S)-propanol (isomer D').

The rodenticidal compositions of the present invention comprise as a rodenticidally active ingredient only those isomers which are less hazardous to non-target species. In the case of compounds of formula II these are the isomers having the (1R,3R) or (1S,3S) configuration, whereas in the case of the compounds of formula I these are the isomers having the (1R,3S) or (1S,3R) configuration. Preferably the active ingredient is a racemic mixture of the (1R,3R) and (1S,3S) isomers of a compound of formula II or the (1R,3S) and (1S,3R) isomers of a compound of formula I. More preferably the active ingredient is selected from the following racemic mixtures:

(a) isomers C and D brodifacoum (i.e. (±)-transbrodifacoum)
(b) isomers C' and D' of bromadiolone
(c) 3R-(biphenyl-4-yl)1R-(4-hydroxycoumarin-3-yl)-1,2,3,4-tetrahydronaphthalane and 3S-(biphenyl-1-yl)-1S-(4-hydroxycoumarin-3-yl)-1,2,3,4-tetrahydronaphthalene (i.e. (±)trans-difenacoum).
(d) 1R-(4-hydroxycoumarin-3-yl)-3R-[4-(4-trifluoromethylbenzyloxy)phenyl]-1,2,3,4-tetrahydronaphthalene and 1S-(4-hydroxycoumarin-3-yl)-3S-[4-(4-trifluoromethylbenzyloxy)phenyl]-1,2,3,4-tetrahydronaphthalene (i.e. the (±)-trans product).

The compositions according to the invention are distinguished from known rodenticidal compositions of 3-substituted-4-hydroxycoumarins by being substantially free of other isomers. By "substantially free" is meant less than 10% by weight and preferably less than 5% by weight of any other isomer or isomers.

In other respects the rodenticidal compositions are formulated in the same manner as those previously described, e.g. as baits in which the diluent or carriers comprises an edible rodent attractant material such as bran, wheat flour and the like, or as tracking powders which are intended to become attached to the rodent's fur and to thereafter be ingested during the grooming process, or as wax blocks or brittle plastic formulations designed to be gnawed by the rodents. All of these variants are well known and have been described elsewhere.

Such compositions contain a rodenticidally effective amount of the chosen isomer of the 3-substituted-4-hydroxycoumarin. Whereas the actual amount present will vary according to the type of formulation and intended target rodent species, suitable bait formulations of trans brodifacoum may contain from 25 to 250 parts per million by weight, and preferably from 50 to 100 parts per million. As a general rule, and since there is apparently no marked difference in rodenticidal activity between the (1R,3R)/(1S,3S) pair of enantiomers and the (1R,3S)/(1S,3R) pair of enantiomers, formulations can be prepared using the same weight percentage of active ingredient of the chosen pair of isomers as would have been recommended for the total isomer mixture used hitherto.

In a further aspect therefore the invention provides a process for the preparation of a composition in the form of a rodenticidal bait formulation which comprises the steps of (a) separating the desired isomer or isomers from any other isomers (b) mixing the thus separated isomer or isomers with an edible carrier so that the formulation contains a rodenticidally effective amount of the said separated isomer or isomers, and if desired, forming the composition into discrete shaped portions, such as pellets or granules.

In a further aspect the invention also comprises a method of reducing a rodent population at a locus frequented by the rodents which comprises placing an invention composition at the locus in such a manner that the composition is accessible to the rodents.

The methods of using the compositions are no different from those which are well known in the art for the use of known anticoagulant compositions. These have been reviewed by Meehan (loc.cit.), see especially pp. 293–329 and the references therein.

The active ingredients for use in the compositions of the invention may be obtained by separation of the required isomers from the mixture of isomers usually obtained for manufacture. The preparation of such isomer mixtures is described in U.S. Pat. Nos. 3,764,693, 4,035,505 and published UK patent application No. 2126578A. The separation of the required isomers may be achieved by, for example, solvent crystallisation techniques, or by chromatographic means, for example that described by Koubec et al, J. Assoc. Off. Anal. Chem., 1979, 62(6), pp. 1297–1301, where a high pressure liquid chromatographic technique was used for brodifacoum.

The method and compositions of the invention may be used to combat and control a wide range of rodent pests, including the following commensal species, *Rattus rattus* (Ship rat, Roof rat, Ricefield rat, Fruit rat) *Rattus norvegicus* (Norway rat, Brown rat) *Mus musculus* (House mouse) as well as non-commensal species which occur particularly as pests of agricultural crops or stored produce in various parts of the world, such as for example voles of the family Crecetidae including Microtus spp. such as *M. agrestis*, and Arvicola spp. such as *A. terrestris*, rats and mice of the family Muridae, including Apodemus spp. such as *A. sylvaticus, Acomys caharinus*, Akodon spp., *Arvicanthis nilotica, Holochilus braziliensis, Mastomys natalensis, Mus booduga, Mus platythrix*, Neotoma spp., Peromysans spp., *Rattus exulans, Rattus maltata, Rattus tiomanicus, Sigmodon hispidus*, and other rodents such as *Nesokia indica, Tatera indica*, Spermophilus spp., Meriones spp., Eutamias spp., Citellus spp., Bandicota spp., *Cricetus cricetus, Ondatra zibetheca*, and *Myocastor coypus*, although this is not intended to be an exhaustive list. Meehan (loc. cit) reviews the economic damage caused by many of these rodent pests.

The compositions and methods of the invention may be successfully used to control rodents whilst minimising the hazard to non-target species as compared with the use of known compositions. Thus pheasants (*Phasianus colchicus*) fed with pelleted rodenticidal formulations of a racemic mixture of isomers C and D of brodifacoum had a much higher survival rate than those fed with a mixture of all four isomers (A, B, C and D at approximately 1:1:1:1 ratio). This illustrates the improved safety of the invention compositions in the case of accidental ingestion of rodenticide bait by a non-target species. Similarly, cats fed on a diet designed to similate the effect of eating a rodenticidally contaminated carcase in which the rodenticide was the mixture of isomers C and D of brodifacoum showed no mortality, the only effect noted being a temporary increase in prothrombin time which returned to normal after a short period. However, cats fed with a similar diet containing the corresponding quantity of all four brodifacoum isomers showed increased prothrombin times which did not return to normal and eventually led to 100% mortality.

This, and other evidence from the analysis of the relative proportions of the cis and trans isomers present in carcasses of target and non-target species, indicates that rapid depuration of isomers C and D of brodifacoum is taking place, presumably by selective metabolism, whereas isomers A and B are not metabolised at a sufficient rate to avoid the lethal consequences. Species in which this selective depuration has been noted include scavanging and preditor mammals such as foxes and cats, and birds such as hawks, owls and crows. Thus if non-target species such as these consume the carcasses of rodents which have been killed by the use of the invention compositions they will be able to metabolise the residues of the active ingredient and not be at risk through bioaccumulation of a toxic dose by subsequently consuming further contaminated carcasses.

In some cases rodents themselves appear to be able to selectively depurate some isomers. However, even though this can be demonstrated to have occurred the rodents do not appear to be able to avoid the lethal effects of having consumed the rodenticide. Thus the compositions of the invention are still effective rodenticides even though some depuration occurs in the period after ingestion. This means that the toxic residues will already have been reduced to some extent in the tissues of the rodent, leaving a smaller residue to be metabolised by any scavanging mammal or bird which consumes the rodent carcass. Rodents which can depurate the active ingredient of the invention compositions in this way include voles, cotton rats, and pocket gophers.

Although the exact mechanisms by which selective depuration of some isomers of 3-substituted-4-hydroxycoumarin rodenticides occurs is not fully understood the difference in the rates of depuration as between different isomers is clearly associated with the conformational differences between the (S,S) and (R,R) configuration of one enantiomer pair and the (S,R) and (R,S) configuration of the other enantiomer pair in relation to the active sites of the metabolising enzymes involved in the process. In such a group of closely similar compounds it may be assumed that isomers of different compounds having similar configurations will behave similarly under the influence of metabolic processes. The scope of the invention thus embraces all such 3-substituted-4-hydroxycoumarin rodenticides capable of existing in more than one stable isomeric form wherein any isomer exhibits a similar conformation to that of those specifically named herein as being preferred active ingredients of the rodenticidal compositions of the invention.

The examples which follow are illustrative of the invention but the spirit and scope of the invention are not intended to be limited thereby.

EXAMPLE 1

Technical grade brodifacoum (analysed by an absorption HPLC technique as of 99.3% purity and containing 58.3% of the cis-isomer and 41.0% of the trans-isomer) was separated into its cis and trans components by a preparative HPLC technique using a Waters Associates liquid chromatographic apparatus. (System 500 with prep-PAK-500 column cartridges containing silica gel (80 m) absorbent and a mobile phase of petroleum spirit (boiling range 40°-60° C.)/diethyl ether/glacial acetic acid in the ratio 70:30:0.4). The residue from each collected fraction was subjected to further purification by preparative HPLC using the same mobile phase. The solvent was removed from the two final fractions and these were shown by 100 MHz proton nuclear magnetic resonance spectroscopy to contain the cis and trans isomers respectively each substantially free from the other isomer.

EXAMPLE 2

An approximately 1:1 mixture of the cis and trans isomers of 1-(4-hydroxycoumarin-3-yl)-3-[4-(4-trifluoromethylbenzyloxy)phenyl]-1,2,3,4-tetrahydronaphthalene in the form of a viscous oil (13.0 g) was dissolved in ethanol (250 cm$^3$) at the ambient temperature and the solution kept in an open flask at the ambient temperature for 3 days during which time some of the ethanol evaporated and some precipitation of a solid material occurred. This was collected by filtration and dried to give trans-1-(4-hydroxycoumarin-3-yl)-3-[4-(4trifluoromethylbenzyloxy)phenyl]-1,2,3,4-tetrahydronaphthalene (containing 7% by weight of the cis-isomer, 1.5 g), melting point 153°–155° C. The filtrate was concentrated by removal of the ethanol by evporation under reduced pressure. The residual oil was then dissolved in boiling ethanol (100 cm$^3$) and the solution allowed to cool to 35° to 40° C. and maintained at this temperature whilst a precipitate formed rapidly. This was collected by filtration and dried to give cis-1-(4-hydroxycoumarin-3-yl)-3-[4-trifluoromethylbenzyloxy)phenyl]-1,2,3,4-tetrahydronaphthalene (containing 5% by weight of the transisomer, 5.5 g) melting point 183°–184.5° C.

The residue obtained from the filtrate was eluted through a silica column (using chloroform as eluent) to give a product (3.3 g) containing 85% of the trans-isomer and 15% of the cis-isomer.

EXAMPLE 3

This Example compares the rodenticidal efficacy of an invention composition comprising isomers C and D of brodifacoum (composition I) and a similar composition comprising all four isomers of brodifacoum (Composition II). Each composition was used in the form of edible pellets comprising for each comparison the same weight of each active ingredient, and each group of rodents was fed at the same rate expressed as milligrams of active ingredient per kilogram of body weight. The following results were obtained.

| (a) Albino Norway Rat (*Rattus norvegicus*) | | |
|---|---|---|
| | Composition I | Composition II |
| LD$_{50}$ mg/kg | 0.30 | 0.31 |
| Range | 0.24–0.34 | 0.27–0.36 |
| Average time to death (days) | 6.6 ± 1.8 | 6.5 ± 1.3 |
| Palatability vs. Standard EPA diet % acceptance | 65.6 ± 15.3 | 67.8 ± 22.3 |
| % mortality | 100 | 100 |

| (b) Meadow vole (*Microtus pennsylvanicus*) | | |
|---|---|---|
| | Composition I | Composition II |
| LD$_{50}$ mg/kg | 0.26 | 0.18 |
| Range | 0.12–0.39 | 0.10–0.25 |
| Average time to death (days) | 6.7 | 7.3 |

| Species | Composition | Average amount consumed (mg/kg) | Mortality (no. dead/no. intest) | Average time to death (days) |
|---|---|---|---|---|
| Wild Norway Rat | I | 3.62 ± 0.77 | 10/10 | 5.5 ± 1.7 |
| (*Rattus norvegicus*) | II | 3.60 | 8/8 | 4.8 ± 2.2 |
| Common Rat | I | 2.19 ± 1.15 | 8/10 | 8.0 ± 1.6 |
| (*Sigmodon hispidus*) | II | 2.0 | 3/4 | 7.3 ± 4.2 |
| 13-Lined Ground Squirrel | I | 1.99 ± 0.26 | 6/10 | 10.2 ± 1.9 |
| *Spermophilus* (Citellus) *tridecemlineatus* | II | 2.0 | 1/3 | 13 |
| Richardson Ground Squirrel | I | 2.54 ± 1.23 | 10/10 | 6.3 ± 2.4 |
| *Spermophilus* (Citellus) *richardsoni* | II | 2.5 | 4/4 | 6.7 ± 1.6 |
| Roof rats | I | 2.73 ± 1.31 | 10/10 | 5.9 ± 1.0 |
| (*Rattus rattus*) | II | 2.6 | 4/4 | 6.0 ± 0.7 |
| Deer Mouse | I | 5.58 ± 1.07 | 8.1 ± 1.8 | |
| | | 17/20 | | |
| (*Peromysans maniculatus*) | II | 5.6 | 4/4 | 6.5 ± 3.3 |
| Wild House Mouse | I | 13.89 ± 8.29 | 7/10 | 7.1 ± 2.1 |
| (*Mus musculus*) | II | 14.0 | 7/10 | 5.3 ± 1.8 |

(c) Various species (Table 1)

EXAMPLE 4

This Example illustrates the selective depuration of the active ingredient of the invention compositions by meadow voles (*Microtus penusylvanicus*).

Fasted wild voles were given pellets containing 10 ppm of mixture (approximately 1:1:1:1 by weight) of isomers A, B, C and D of brodifacoum until they had consumed 0.54 mg of active ingredient per kilogram of body weight. Voles were killed at 0, 1, 2, 3, 4, 5 and 14 days after dosing and the relative amounts of the A, B isomer pair and the C, D isomer pair remain in the vole tissue determined by chromatographic means. The results, given in Table II below, indicate rapid depuration of the C, D isomer pair, whereas the A, B isomer pair is retained in the tissue. The half life of the C, D isomer pair is calculated as ca. 24 hours whereas that of the A, B isomer pair is in excess of 14 days.

TABLE II

Amounts of isomer pairs recovered from the tissue (expressed as mg/kg).

| | Days after dosing | | | | | |
|---|---|---|---|---|---|---|
| | 0 | 1 | 2 | 3 | 4 | 5 |
| Isomers A and B | 0.15 | 0.147 | 0.114 | 0.114 | 0.123 | 0.101 |
| Isomers C and D | 0.122 | 0.052 | 0.024 | 0.014 | 0.011 | 0.005 |
| Ratio | 0.818 | 0.354 | 0.211 | 0.123 | 0.089 | 0.05 |

EXAMPLE 5

A bait formulation may be prepared by admixing oatmeal with an acetone slurry of trans-brodifacoum and, after air drying the mixture, diluting with further oatmeal until the product contains 100 parts per million by weight of trans-brodifacoum.

EXAMPLE 6

This Example illustrates rodenticidal compositions according to the invention. The active ingredient in each case is selected from ($\pm$)-trans-brodifacoum, the racemic mixture of isomers C' and D' of bromadiolone and the trans-isomer obtained by the process of Example 2. Compositions A, B and C are intended for use without further dilution. Compositions D and E are examples of concentrates which are more convenient for storage and transportation and which can be diluted with an edible carrier, such as wheat meal, maize meal or oatmeal, to give an active ingredient content within the range 25 to 250 parts per million.

A. Bait formulation

| Ingredients | Wt % |
|---|---|
| Active ingredient | 0.005 |
| Chlorinated phenols (preserving agent) | 0.005 |
| Synthetic wax (hydrophobic agent) | 5.000 |
| Protein hydrolysate (rodent attractant) | 2.500 |
| Powdered chalk | 4.500 |
| Polyethylene glycol (moisture retaining agent) | 0.500 |
| Prussian blue (visible dye) | 0.250 |
| Wheat meal | to 100.000 |

This composition may be used as a powder or may be compressed into pellets.

B. Bait formulation

| Ingredient | Wt % |
|---|---|
| Active ingredient | 0.005 |
| Vegetable oil | 5.000 |
| Maize meal/oat meal mixture (3:1) | 90.000 |
| Sucrose | to 100.00 |

C. Wax block formulation

| Ingredient | Wt % |
|---|---|
| Active ingredient | 0.005 |
| Polyethylene glycol | 0.050 |
| Maize meal | 55.000 |
| Sucrose | 5.000 |
| Prussian Blue | 0.250 |
| Paraffin wax | to 100.000 |

D. Liquid Concentrate

| Ingredient | Wt % |
|---|---|
| Active ingredient | 0.25 |
| Vegetable oil | to 100.00 |

E. Powder Concentrate

| Ingredient | Wt % |
|---|---|
| Active ingredient | 0.1 |
| Mineral oil | 10.0 |
| Kaolin | to 100.0 |

I claim:

1. An improved rodenticidal bait composition consisting essentially of an edible solid carrier material and a rodenticidally effective amount of a rodenticide consisting essentially of the trans isomer of the 3-substituted-4-hydroxy coumarin compound of the formula:

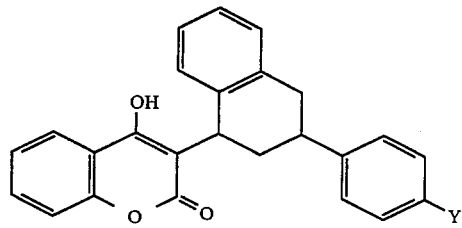

wherein Y is 4-bromophenyl, said trans isomer, when compared with the cis isomer of said 3-substituted-4-hydroxycoumarin compound being significantly less persistently retained in the tissues of non-rodent mammalian or avian species likely to consume either rodentical bait or poisoned rodent carcasses, said composition being substantially free of the cis isomer whereby the risk to non-target species arising from accidental ingestion of the rodenticide is minimized.

2. A composition according to claim 1 wherein the trans isomer is a racemic mixture of the enantiomeric pair of isomers consisting of 3R-(4'-bromobiphenyl-4-yl)1R-(4-hydroxycoumarin-3-yl)-1,2,3,4-tetrahydronaphthalene and 3S-4(4'-bromo-biphenyl-4-yl)1S-(4-hydroxycoumarin-3-yl)-1,2,3,4-tetrahydronaphtalene, said composition being substantially free from any cis isomer of the said 3-substituted-4-hydroxycoumarin.

3. A method of reducing a rodent population at a locus frequented by rodents which comprises placing an effective amount of a composition according to claim 1 at the locus in such a manner that the composition is accessable to the rodents.

* * * * *